(12) United States Patent
Appoldt et al.

(10) Patent No.: US 7,651,664 B2
(45) Date of Patent: Jan. 26, 2010

(54) APPARATUS AND METHOD FOR PREPARING SOLUTIONS AND/OR DILUTIONS IN THE LABORATORY

(75) Inventors: Yvonne Appoldt, Zürich (CH); Jörg Burmester, Zürich (CH); Matthias Kläy, Rapperswil (CH)

(73) Assignee: Mettler-Toledo GmbH, Greifensee (CH)

( * ) Notice: Subject to any disclaimer, the term of this patent is extended or adjusted under 35 U.S.C. 154(b) by 1031 days.

(21) Appl. No.: 10/786,580

(22) Filed: Feb. 26, 2004

(65) Prior Publication Data
US 2004/0171171 A1   Sep. 2, 2004

(30) Foreign Application Priority Data
Feb. 27, 2003   (EP)   ................................. 03100489

(51) Int. Cl.
*B01L 3/02* (2006.01)
(52) U.S. Cl. .................. 422/100; 422/99; 436/163; 436/179; 700/239; 700/265
(58) Field of Classification Search .................. 422/62, 422/67, 99, 100, 105, 116; 436/43, 50, 54, 436/163, 174, 179; 700/239–241, 265–267; 702/19, 22, 23, 50
See application file for complete search history.

(56) References Cited

U.S. PATENT DOCUMENTS

| 5,402,834 | A | * | 4/1995 | Levin et al. ..................... 141/83 |
| 5,460,209 | A | * | 10/1995 | Jandura et al. ................. 141/83 |
| 5,544,684 | A | * | 8/1996 | Robinette, III ................ 141/83 |
| 5,746,238 | A | * | 5/1998 | Brady et al. .................... 137/3 |
| 5,938,080 | A | * | 8/1999 | Haaser et al. ................. 222/144 |
| 6,120,175 | A | * | 9/2000 | Tewell ........................ 366/140 |
| 6,194,670 | B1 | | 2/2001 | Reichmuth et al. |
| 6,763,860 | B2 | * | 7/2004 | Jungmann et al. ........... 141/104 |
| 6,778,917 | B1 | * | 8/2004 | Jansen .......................... 702/45 |
| 7,110,861 | B2 | * | 9/2006 | Nelson et al. ............... 700/265 |

(Continued)

FOREIGN PATENT DOCUMENTS

EP   0 651 306 A1   5/1985

(Continued)

*Primary Examiner*—Jill Warden
*Assistant Examiner*—Dwayne K Handy
(74) *Attorney, Agent, or Firm*—Buchanan Ingersoll & Rooney PC (57) ABSTRACT

A device is disclosed for preparing a solution of a solid with a liquid and/or a dilution of a liquid with another liquid includes a balance with a weighing pan, a display- and operating unit, a processor, a storage memory, and a data interface. The device includes at least one electronic dosage delivery device for liquids, in particular an electronic pipette, with a microprocessor, a memory unit, and a data interface, so that a communication can be established between the respective data interfaces of the balance and the at least one electronic dosage delivery device. An identifier element signals when the electronic dosage delivery device has been selected. A program is configured to perform calculations in the processor of the balance based on instructions given by the attendant, based on substance data stored in the memory of the balance and in certain cases based on weighing results. The program can select a dosage delivery device and set the selected dosage delivery device for the liquid volume that is to be taken in and/or dispensed.

34 Claims, 4 Drawing Sheets

U.S. PATENT DOCUMENTS 7,206,664 B2 * 4/2007 Schmid ........................ 700/239
2002/0020569 A1 2/2002 Eigenmann et al.

FOREIGN PATENT DOCUMENTS

| | | | |
|---|---|---|---|
| EP | 0 999 432 A2 | 10/1999 | |
| WO | WO83/02761 | 8/1983 | |
| WO | WO02/073142 A1 | 9/2002 | |

* cited by examiner

APPARATUS AND METHOD FOR PREPARING SOLUTIONS AND/OR DILUTIONS IN THE LABORATORY

CROSS REFERENCE TO RELATED APPLICATIONS

This application claims priority under 35 U.S.C. §119 to European Application 03100489.8 filed in Europe on 27 Feb. 2003, the entire contents of which are hereby incorporated by reference in their entirety.

BACKGROUND

An apparatus is disclosed for preparing a solution of a solid with a liquid and/or for diluting a liquid with a further liquid by means of a balance and at least one electronic dosage delivery device for liquids, in particular an electronic pipette, where the arrangement includes a means of communication between the balance and the at least one electronic dosage delivery device. A method involving the use of the apparatus for preparing solutions and/or dilutions in a laboratory is also disclosed, as is a program through which the apparatus carries out the method.

Dosage delivery devices, in particular hand-held electronic dosage delivery devices such as electronic pipettes, burettes, and other dispensers, are widely used in laboratories. Applications for such devices are found in all processes where a defined quantity of a liquid has to be added, for example in the preparation of solutions or dilutions. In most cases, the devices are used for routine laboratory procedures where a wide diversity of different end products are to be produced with different chemicals, but where such procedures usually occur one at a time, i.e., not frequently enough that, e.g., the use of a laboratory robot could be economically justified. Nevertheless, it is desirable to simplify and automate electronic dosage delivery systems and thereby improve the ways in which operational procedures, operating parameters, and programs or program parts can be influenced and controlled and to provide better assurance of the resulting data.

The European Patent Application EP 0 999 432 A1 describes a method of operating an electronic dosage delivery system and also describes a dosage delivery system of the kind envisaged by the method, with a handheld electronic dosage delivery device such as, e.g., an electronic pipette with a data interface through which a communication to the data interface of a data processing system can be implemented by way of an electronic data transfer connection. The data communication provides read/write access from the data processing system to a memory of the handheld dosage delivery device, so that memory parameters specific to the instrument type and/or to the individual instrument and/or to the application, and/or program routines for application procedures and/or the program of the controller device of the handheld electronic dosage delivery device and/or at least a program part can be written into or read out from the memory of the handheld dosage delivery device, and/or the handheld dosage delivery device can be remote-controlled. Remote control of the dosage delivery device is advantageous for dosage-dispensing procedures, e.g., if the handheld dosage delivery device is used within a superordinate automation process, or to use the handheld dosage delivery device in a contaminated environment without endangering the person attending to the process. By means of a program routine for running application procedures, it is possible, e.g., to control the intake, mixing, and dispensing of defined quantities of liquid, or to carry out a sequence of diluting steps, where the dispensed dosage volume is halved in each successive step. As a further possibility, an application routine of this kind can also be transferred into the handheld dosage delivery device.

Besides electronic dosage delivery devices for liquids, in particular handheld devices such as pipettes or dispensers, routines for preparing solutions and/or dilutions in the laboratory also involve the use of electronic balances. For example in the case of preparing a solution, the first step is weighing-in a defined quantity of a solid substance into a container on the balance. Based on a desired concentration of the solution, one calculates the quantity of the liquid solvent that needs to be added, e.g., by means of a pipette or a measuring cylinder or an other container. It needs to be noted, however, that in order to obtain a desired end result, this procedure requires a sufficiently accurate accounting for parameters of the liquid solvent such as temperature, density, coefficient of volume expansion and/or purity of the solvent. As a rule, the person who was given the task of preparing the solution and/or dilution makes these calculations by means of a simple laboratory computer or pocket calculator. In most cases, a calculation of this kind is time-consuming and entails the risk of calculation errors. Furthermore, there is no control mechanism to check whether the resulting solution and/or dilution is plausible in view of the data entered into the calculations and to what extent the end product lies within the target range of the desired concentration.

It is also common practice to prepare a quantity of solution that matches the available container. This means that in preparing a solution, e.g., in a measuring flask of a given volume, the substance quantities entering into the solution have to be calculated and weighed in under the constraint that the volume of the measuring flask determines the volume of the solution or dilution to be prepared. Often, this has the consequence that an excess quantity of solution is prepared which, if it is not otherwise needed, has to be safely disposed of.

The International PCT Application WO 02/073142 A1 describes an apparatus for mixing substances, in particular dyestuff components, which includes units that are integrated in a measuring device—in particular in a balance—such as a processor unit, a local memory unit for the storing of mix formulas, a display unit and an input unit. The balance measures the quantities of component substances that are added to a container sitting on the balance pan. In the case of an automated process, the balance controls valves that are connected to supply conduits, in accordance with the relative proportions of the substances to be mixed. The actual weight measured by the balance is continuously compared to a target value that is based on a mixture formula, and the result of the comparison is used to control the inflow of the substance that is to be added to the container.

The European Patent Application EP 0 651 306 A1 discloses an apparatus for preparing solutions, where a container that is to receive the components of a solution is resting on the pan of a balance. The solvent liquid is added through a valve connected to a conduit through which the solvent is supplied from a solvent reservoir by means of a pump. The valve and the pump as well as the balances are monitored by a control unit. Based on a procedure stored in the control unit, an indication of limit values in the form of weight values for the addition of solvent are presented to the individual attending the apparatus. Based on the weight data delivered by the balance, which are graphically presented in the form of moving bar in an output unit, the attendant is guided to stop the inflow of solvent when the weight value is within the indicated limits.

The International PCT Application WO 83/02761 A1 likewise discloses an apparatus for the preparation of solutions, where a control unit and a balance belong to the apparatus and where the solvent liquid is added through valves connected to a conduit through which the solvent is supplied from a solvent reservoir by means of a pump. The delivery of the desired quantity of solvent occurs manually or automatically in accordance with a control program, as the measured weight values are continuously transferred to the control unit and indicated on an output unit. The valves have different flow rates, so that at the beginning of a solvent delivery the valve with the higher flow rate is opened and as the weight value for the total weight of the solution approaches its target value, the valve with the lower flow rate is used for the end of the solvent delivery.

The aforementioned references disclose methods of preparing a mixture or a solution where the delivered dose of the solvent or an additional component is controlled through a comparison of an actual value to a target value in an arrangement with a substantially fixed installation of the means for delivering the dosage quantities.

SUMMARY

An apparatus is disclosed for preparing a solution of a solid with a liquid and/or for preparing a dilution of a liquid with another liquid, which is simpler to operate and offers higher degrees of assurance and flexibility. A simple and safe method are disclosed as well as a program for preparing a solution of a solid with a liquid and/or for preparing a dilution of a liquid with another liquid.

The concepts of an apparatus or method for preparing a solution of a solid with a liquid and/or for preparing a dilution of a liquid with another liquid include the possibility of using more than one solid or more than one liquid solvent or diluent.

An apparatus for preparing a solution of a solid with a liquid and/or a dilution of a liquid with another liquid includes a balance that has a weighing pan, a display- and operating unit, a processor, a storage memory, and a data interface. The apparatus further includes at least one electronic dosage delivery device for liquids, in particular an electronic pipette, which is equipped with a microprocessor, a storage memory, an identifier element that signals when the electronic dosage delivery device has been selected, and a data interface. The concept of the apparatus includes the capability for a communication between the data interface of the balance and the data interface of the electronic dosage delivery device. The balance has the capability to run a program for preparing a solution of a solid with a liquid and/or a dilution of a liquid with another liquid. The program can perform calculations in the processor of the balance based on instructions entered by the attendant of the apparatus, further based on substance data stored in the memory of the balance, and in some cases based on obtained weighing results; it can select which dosage delivery device out of an available selection is to be used; and it can set the delivery device for the liquid volume that is to be aspirated and/or dispensed.

A method for preparing solutions and/or dilutions in a laboratory involves the use of the apparatus of the foregoing description. The method includes the running of a program in the processor of the balance, wherein the program performs calculations based on instructions entered by the attendant, further based on substance data stored in the memory of the balance, and in some cases based on obtained weighing results; wherein the program selects which dosage delivery device out of an available selection is to be used; wherein the program also enters the setting in the dosage delivery device for the liquid volume that is to be aspirated and/or dispensed; and wherein the program activates the identifier element of the selected electronic dosage delivery device.

The apparatus as well as the method for preparing solutions and/or dilutions have the purpose to assist the attendant operator in his or her everyday work activities in the laboratory. In addition to simplifying the procedure and thereby saving time, the preparation of solutions and/or dilutions in the laboratory is made notably safer. For example, the attendant no longer has to adjust an electronic pipette manually, as the program automatically sets the pipette to the required volume.

As the calculations that are part of the process are performed in the balance, the risk of calculation errors is drastically reduced and the level of assurance is increased in comparison to the existing methods described hereinabove.

In an application where solutions and/or dilutions are prepared with very expensive materials, an exemplary method allows additional substances to be weighed and added in very precise doses so that there is no deficiency nor excess in the amount of solution and/or dilution produced. As a result, there is no waste, nor is it necessary to perform the procedure a second time to correct the discrepancy. Ultimately, this can result in cost savings.

In an exemplary the apparatus and method, an electronic dosage delivery device, in particular a handheld electronic dosage delivery device such as an electronic pipette, functions as a kind of liquid-dispensing spatula. As the processor- and memory capacity of the electronic dosage delivery device is relatively small, it was found practical to control the dosage delivery device from a superordinate system, in this case from the balance, particularly for the reason that the balance has the capability to measure the relevant quantities, i.e., the weights of the substances involved, with a very high degree of accuracy. Furthermore, an electronic balance is equipped with a display- and operating unit where entries can be made with considerably greater convenience than, e.g., through the operating buttons on a pipette. Likewise, a menu of program selections or an instruction for a work procedure is more suitably represented on the display screen of a balance rather than on the limited display space of a pipette.

Exemplary embodiments further make use of the fact that an electronic balance can communicate and interact with other laboratory instruments through data interfaces. This capability leads to the requirement to optimize a dosage delivery device for liquids in regard to its communication with a balance, so that the dosage delivery device can meet the target values prescribed by the balance in the preparation of solutions and/or dilutions in the laboratory. It is nevertheless desirable for the balance as well as the dosage delivery device to be capable of operating independently, i.e., in applications where they are not part of an apparatus of the kind described above.

In an exemplary embodiment, a code reader device is connected for communication with the balance. The code reader device serves at least in part for the data entry and in particular for the identification of the chemicals that are to be used in a procedure.

Preferences, instructions and confirmations are entered by the attendant through the display- and operating unit of the balance.

An exemplary embodiment of the apparatus is equipped with a recording device, in particular an activity-log printer, a label printer and/or a code printer, which is interfaced with the balance. The printer provides standardized activity logs for the attendant, so that the work activities are traceable. Furthermore, the container with the completed solution or dilution can be identified with a printed label or code in an unambiguous and error-free manner.

According to an exemplary embodiment, the memory of the balance includes a database in which data and/or parameters of substances are stored so that they can be recalled.

In a further embodiment, the balance can be connected for communication with a laboratory information management system. In an arrangement of this kind, information regarding the parameters of the substances to be used can be recalled from the management system, and a record about a completed solution or dilution can be stored in the information management system so that the record will be available for further use if necessary.

According to an exemplary variation, the balance can be connected to a data-processing system, in particular to a personal computer or to a palmtop, or it can be connected to a computer that is part of a network. The computer or network can have a database in which data and/or parameters of substances are stored so that they can be recalled by the balance. It is also possible that the balance moves data into outside storage in the connected system, or that the data entry takes place through a data input unit of a connected data-processing system.

An electronic dosage delivery device for liquids which is part of an exemplary apparatus for preparing solutions and/or dilutions includes an identifier element. In performing the process of preparing solutions and/or dilutions, the program selects a suitable dosage delivery device from an available selection of electronic dosage delivery devices for liquids and thereby activates the identifier element of the selected device while the latter is being set for the liquid volume to be taken in and/or dispensed. The attendant can thus be assured of having selected the correct dosage delivery device for the application.

In a further exemplary embodiment, the balance registers the weight of a solution and/or dilution after it has been completed and performs a plausibility check. The balance represents a second, independent measuring instrument within the apparatus for preparing solutions and/or dilutions, a fact that is advantageously used on the one hand for quantitative determinations of high precision, e.g., in the processing of very expensive substances or of small volumes, and on the other hand as a means for confirming and checking the results. Consequently, the level of assurance is increased in the performance of the production process itself as well as for the result of the process.

A recording device that is interfaced with the balance serves to produce an activity log of a completed and/or prematurely terminated preparation of a solution of a solid with a liquid and/or a dilution of a liquid with a further liquid. This assures traceability of the process by logging all activities performed by the attendant as well as recording the substances used in the process. Also, by automatically generating an unmistakable means of identification, for example an adhesive label which can be applied to the container used in the preparation of solutions and/or dilutions, the level of assurance in the operation of the laboratory is increased and the risk of a mix-up is prevented.

The operating sequences to be performed under the methods disclosed herein are freely configurable.

The apparatus for preparing a solution of a solid with a liquid and/or a dilution of a liquid with a further liquid is designed to execute a program which sequentially proceeds through the steps of a work procedure that has been prescribed by an attendant for preparing a solution of a solid with a liquid and/or a dilution of a liquid with a further liquid. The program is configured for using instructions given by the attendant, substance data available from the memory of the balance, and in some cases weighing results that have been determined by the balance. Under the program, calculations are performed, a dosage delivery device is selected from an available selection of dosage delivery devices, the selected dosage delivery device is set for the volume of liquid to be taken in and/or dispensed, and the identifier element of the selected electronic dosage delivery device is activated.

BRIEF DESCRIPTION OF THE DRAWINGS

Further details are presented in the following description of processes and examples that are schematically illustrated in the drawings and also from the presentation of a device for preparing a solution of a solid with a liquid and/or a dilution of a liquid with a further liquid. In the drawings.

DETAILED DESCRIPTION

Figure 1:
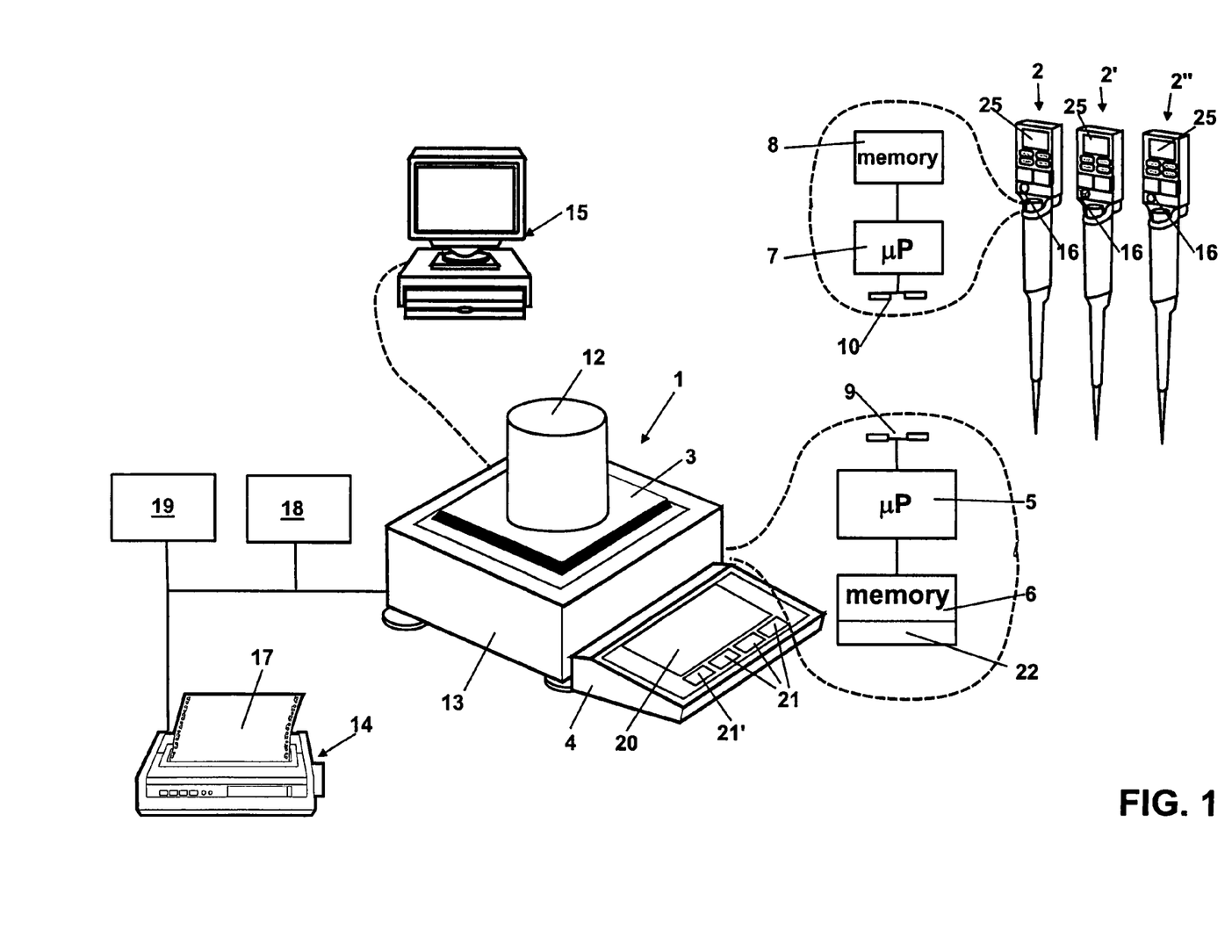
FIG. 1 represents an exemplary for preparing a solution of a solid with a liquid and/or a dilution of a liquid with a further liquid.

FIG. 1 illustrates an example for the layout of a work station with an apparatus for preparing a solution of a solid with a liquid and/or a dilution of a liquid with a further liquid. One of the principal components of the apparatus is a balance 1 with a weighing pan 3 and with a display/operating unit 4. The balance 1 is equipped with a processor 5, a memory unit 6, and a data interface 9, where the physical parts of the data interface can be arranged adjacent to the housing 13 of the balance and exposed to the outside. The apparatus further includes electronic pipettes 2, 2', 2" which are available for selection, where each of the pipettes is designed for a different volume capacity. Each of the pipettes 2, 2', 2" is equipped with a microprocessor 7 and a memory unit 8. The microprocessor 7 is connected to a data interface 10 which can be connected for communication with the data interface 9 of the balance 1. A pair of data interfaces like the pair 9, 10 can be designed for either a cable-based or wireless form of communication. Examples for the latter are a radio connection or an infrared connection, where each of the interfaces 9 and 10 includes a sender as well as a receiver. Each of the available pipettes 2, 2', 2" has an identifier element, e.g., a light-emitting diode 16, that produces an optical signal to identify which among the pipettes 2, 2', 2" is in communication with the balance 1 and/or to indicate when the currently active work program in the processor of the balance has selected for example the pipette 2' as suitable for adding a prescribed solvent or diluent and has adjusted the setting of that pipette if necessary.

As an example of a simple solution, the display field 25 of an electronic pipette could be used as identifier element, in which case the light-emitting diode 16 can be left out. In the example where the pipette 2' has been selected as suitable for adding the solvent or diluent, the display field 25 of the pipette 2' blinks in a way that is noticeable to the attendant. As an alternative, the selected pipette 2' can also produce an audible signal.

The program, which resides in a conventional manner in the microprocessor 7 of a pipette 2, 2', 2" and which enables the pipette to operate, is adapted to the task of enabling the pipette 2, 2', 2" to communicate with a balance 1, so that the pipette is controlled by the balance. The adapted program uses a so-called communications protocol for the communication between the balance 1 and the pipette 2, 2', 2". A corresponding communications protocol is implemented in the balance as a part of the program for the preparation of a solution of a solid with a liquid and/or a dilution of a liquid with a further liquid which is executed primarily in the processor of the balance 1.

The apparatus can be designed to require only a moderate data storage capacity in the memory unit 8 of the electronic pipette 2, 2' 2" and only moderate capabilities in the microprocessor 7, and to control the pipette 2, 2', 2" as a so-called slave instrument entirely from the so-called master instrument that is constituted by the balance 1.

A container 12 is placed on the weighing pan 3 to receive the substances that are to be dissolved and/or diluted, so that they can be weighed by the balance 1. This allows a very accurate determination of the quantity of a first substance for the solution and/or dilution.

The balance 1 is connected to a printer 14 which produces an activity log 17. Additional peripheral devices can be connected to the balance 1, for example a label printer 18 or a code reader 19.

The display- and operating unit 4 of the balance 1 is equipped with entry keys 21 and a screen 20 which can be configured as a pixel-based display. Among other functions that it can perform, the display indicates weighing results, parameter settings of the balance, and auxiliary information including date and time. The screen 20 can furthermore display instructions for performing a work procedure, commonly referred to as a standard operating procedure (SOP). In particular, the screen 20 is designed as a so-called touch screen, so that data entries required in the framework of selected and displayed work procedures, for example a targeted volume or a targeted concentration, or a confirmation of a displayed value, can be entered directly through the display screen 20 and, if applicable, a selection can be made from a program menu. The display- and operating unit 4 also has the capability for configuring new work procedures and/or activity logs 17, in which the process of preparing a solution and/or dilution is recorded.

The data of the chemicals used in the process (solids, solvents, and in some cases other liquids) are stored in a database 22. In particular the properties and substance parameters of the chemicals can be part of the database information. The work procedures for preparing a solution or dilution are likewise stored in the database 22. The work procedures can be created or modified either by the attendant or by a person in charge of the laboratory, in other words they are freely configurable. The database 22 can reside in the memory 6 of the balance 1.

In certain cases, in particular when an increased memory capacity is required, it can also be advisable to connect the balance 1 to a computer 15, which may be a personal computer 15 or a palmtop computer, or a computer that is part of a network, wherein in all cases the computers assist the apparatus for the preparation of a solution and/or a dilution. The last-mentioned optional interfacing connection is represented by a broken line in FIG. 1. In particular, this arrangement offers the possibility to rely on an external database from which the work procedures or substance parameters can be called up by the balance 1 and loaded into the memory 6 of the balance 1, or it offers the possibility to rely on a laboratory information management system (LIMS) in which the data of the prepared solution and/or dilution are stored.

If conventional state-of-the-art procedures are used to prepare a solution of a solid, e.g. a powder, and one or more liquids, the individual preparing the solution needs to be well versed in the properties of the available materials and in the calculations required to determine the concentration in terms of molarity, weight or volume for the solution that is to be prepared. Thus, an individual preparing a solution in a laboratory according to conventional methods has to perform most of the following steps 30 to 40, which are illustrated in the flowchart 2a in the left-hand part of FIG. 2.

Figure 2:
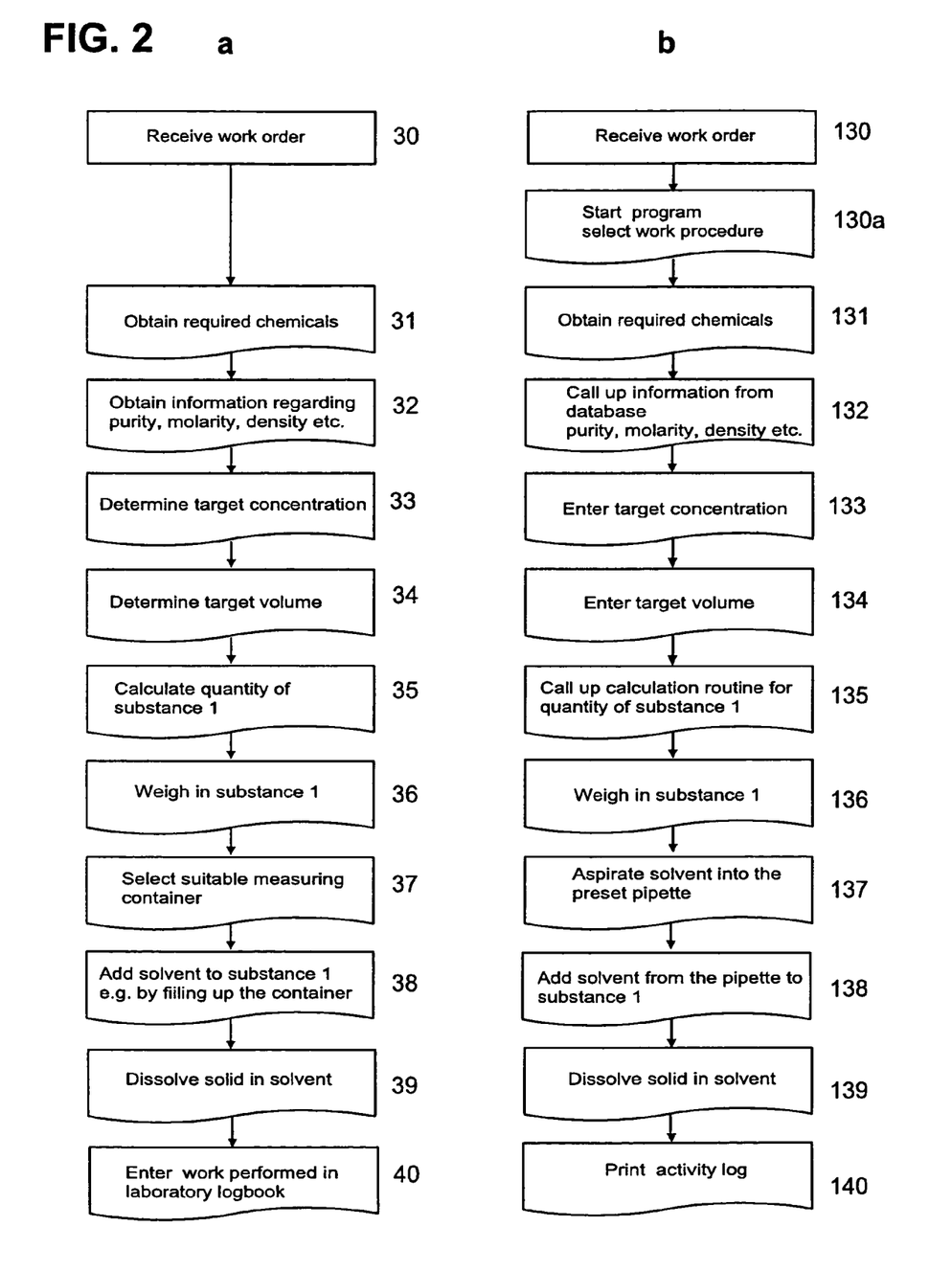
FIG. 2 represents exemplary activities that an attending person has to perform a) in preparing a chemical solution under the state of the prior art in comparison to b) preparing a chemical solution by means of a method as disclosed herein.

- 30 Receiving the work order to prepare a solution of a solid with one or more liquids,
- 31 Selecting and obtaining the required chemicals, i.e., the substance to be dissolved and the one or more solvents.
- 32 Obtaining the information on the chemicals (purity, density, molecular weight, etc.) either from tables, from a database, or from the container label.
- 33 Determining the required concentration of the solution in the desired unit of measure (e.g., weight percent, volume percent, moles per liter). This determination may require certain calculations based on the information and substance parameters found in the preceding step.
- 34 Determining the required volume of the solution to be prepared, which will depend primarily on how much of the solution will be needed for further processes.
- 35 Calculating the quantity of the first substance to be weighed in, which is in most cases a solid, for example a powder, and calculating the volume of the one or more liquids to be added.
- 36 Placing a suitable container on the weighing pan of, e.g., a laboratory balance, canceling the container weight with the tare function of the balance, and precisely weighing the required substance quantity into the container. The weighing accuracy has to conform to the desired accuracy for the concentration of the solution, because in many cases the quantity of solvent to be added has already been calculated beforehand, or because the total quantity is given by the volume of the available measuring container.
- 37 Selecting a suitable measuring container, for example a calibrated measuring flask, and transferring the first substance to the measuring flask.
- 38 Adding the solvent to the container or flask with the first substance, which at this point no longer needs to be resting on the balance pan. The solvent is added either by filling the measuring flask up to its specified volume or by dispensing the targeted amount of liquid from a suitable pipette which has been adjusted beforehand to the required volume, if necessary.
- 39 Assisting the process of dissolution, e.g., by shaking the container or by stirring the contents of the container.
- 40 Entering the work operations performed as well as the chemicals used and their specific parameters in the laboratory logbook and marking the container with the solution.

FIG. 2 allows a comparison between the flowchart 2a representing the foregoing state-of-the-art process and the flowchart 2b representing an example of a process according to an exemplary method for preparing a solution, where the steps 30 to 40 in FIG. 2a are replaced by steps 130 to 140 in FIG. 2b. The entries required in the process according to flowchart 2b are made through the display- and operating unit 4 of the balance 1.

130 Receiving the work order to prepare a solution of a solid with a liquid.

130a Starting the program for the preparation of a solution of a solid with a liquid and/or a dilution of a liquid with a further liquid in the display/operating unit 4 of the balance 1. Selecting a work procedure for preparing a specific solution from a selection of procedures that are predefined in the program and presented as a program menu on the display screen 20.

131 Selecting and obtaining the required chemicals, i.e., the substance to be dissolved and the one or more solvents.

132 Calling up the required information, e.g., by simply pressing a key of the display/operating unit 4 of the balance 1, which causes the program to perform a look-up of the required information on the chemicals in a database 22 which can be stored in the memory 6 of the balance 1 or in some cases in a computer 15 that is interfaced with the balance.

133 Entering the required concentration of the solution in the desired unit of measure. If conversions into different units are required, they are performed automatically by the program.

134 Entering the required volume of the solution to be prepared, which will depend primarily on how much of the solution will be needed for further processes.

135 Calling up the calculation routine for the quantity of the first substance to be weighed in (solid substance), for example by pressing a key 21 as a confirmation that the preceding step of the procedure has been completed. The program performs this calculation based on the information obtained from the database 22, and the result is displayed to the attendant on the screen 20 of the display/operating unit.

136 Placing a suitable container 12 on the weighing pan 3, canceling the weight of the container 12 with the tare function of the balance 1, and precisely weighing the required substance quantity into the container 12. In most cases, i.e., unless a precisely defined target volume is required, the weighed-in quantity needs to match the calculated only approximately, because the quantity of solvent to be added has not yet been calculated at this point. The quantity of solvent to be added is calculated automatically based on the weighing result and based on the substance parameters after a confirming key 21 has been pressed. The program then proceeds to select a suitable pipette 2' from a selection of pipettes 2, 2', 2" that are available at the work station. The selected pipette 2' is identified by a signal, e.g., a blinking light-emitting diode 16, while at the same time the target volume for the solvent is automatically preset in the pipette 2'.

137 Aspirating the solvent into the pipette 2'.

138 Delivering the solvent from the pipette 2' into the container 12 with the first substance while the receiving container 12 remains on the weighing pan 3 of the balance 1.

139 Assisting the process of dissolution, e.g., by stirring the contents of the container 12. In response to pressing a confirmation key 21, the weight of the completed solution is determined by the balance 1, and the result is checked for plausibility in view of the substances weighed in and added and in view of the data and parameters used in the calculations. Also checked is the degree to which the completed solution conforms to the targeted range for the desired concentration and/or volume.

140 Pressing a specified key 21' on the display/operating unit 4 of the balance 1, or a confirmation key, or a touch screen field to enter a print command which causes an activity log 17 to be printed on a printer 14 that is interfaced with the balance. The activity log 17 documents the chemicals used as well as their specific substance parameters, the solution produced, the quantity and volume of the solution, and possibly additional data, such as the name or other identification of the attendant individual who prepared the solution.

It is also possible to combine the steps 132 to 134 if a formulation recipe is already stored in the balance 1, i.e., a work routine in which the substances to be used as well as their respective parameters are already known and the target concentration and target volume are prescribed. Preparing and storing a formulation recipe of this kind can be used, for example, where the same solution or dilution is prepared routinely as a repetitive task.

In order to achieve a higher accuracy, particularly in the mass calculations described in steps 135 and 139, the temperature of the substances used and in particular the temperature of the solution or dilution itself may need to be taken into account in the preparation of the solution or dilution. Given the well-known fact that the density of a substance, in particular of a liquid, is temperature-dependent, the mass of the substances to be weighed in (step 135) as well as the mass of the completed solution in the plausibility check (step 139) can be calculated more accurately.

The temperature of the component substances and/or of the completed solution can be determined, e.g., with a suitable electronic thermometer from which the temperature data can be transmitted to the balance 1. The temperature is subsequently taken into account as a parameter in the calculations.

It is also possible to connect a label printer 18 to the balance 1. In response to a print command, the printer 18 prints a label that can be attached to the container 12 with the solution. In addition, there can be a data transfer connection from the balance 1 to a laboratory information management system (LIMS), through which the relevant data associated with the preparation of a solution are transferred to and stored in the LIMS.

In a variation of the process illustrated in FIG. 2b, a code reader 19 can be connected to the balance 1. In steps 131 and 132 of the method according to the foregoing description, a code attached to the substance container can be scanned, whereby the program is enabled to access the database 22 directly and look up the required data and parameters for the substance without the need for an input by an attendant operator. If desired for assurance purposes, the program can be designed so that it requests a confirmation from the attendant.

An exemplary purpose of the method is to facilitate the work of the attendant operator who prepares the solution. As a special benefit, however, an exemplary method provides a higher level of assurance, first of all by performing the computational steps as a part of the program and thereby preventing calculation errors, and second of all by indicating whether or not the end product is plausible based on the weight of the completed solution. Furthermore, a clear record in a prescribed format is generated, which assures the traceability of the solution, e.g., based on the operating steps that were performed, the chemicals that were used, and the input parameters that entered into the process.

With an exemplary method, one only has to know the desired solution, the specified concentration and the specified volume, and to specify and obtain the required chemicals. The further computing steps and decisions are taken over by the program. As a result, the method also expedites the preparation of solutions through a partial automation of the process. It conforms to the requirements of good laboratory practice and traceability by generating a work record 17. Furthermore, if a label printer 18 is attached to the balance 1, a label can be printed to identify the container 12 with the solution that was prepared.

Figure 3:
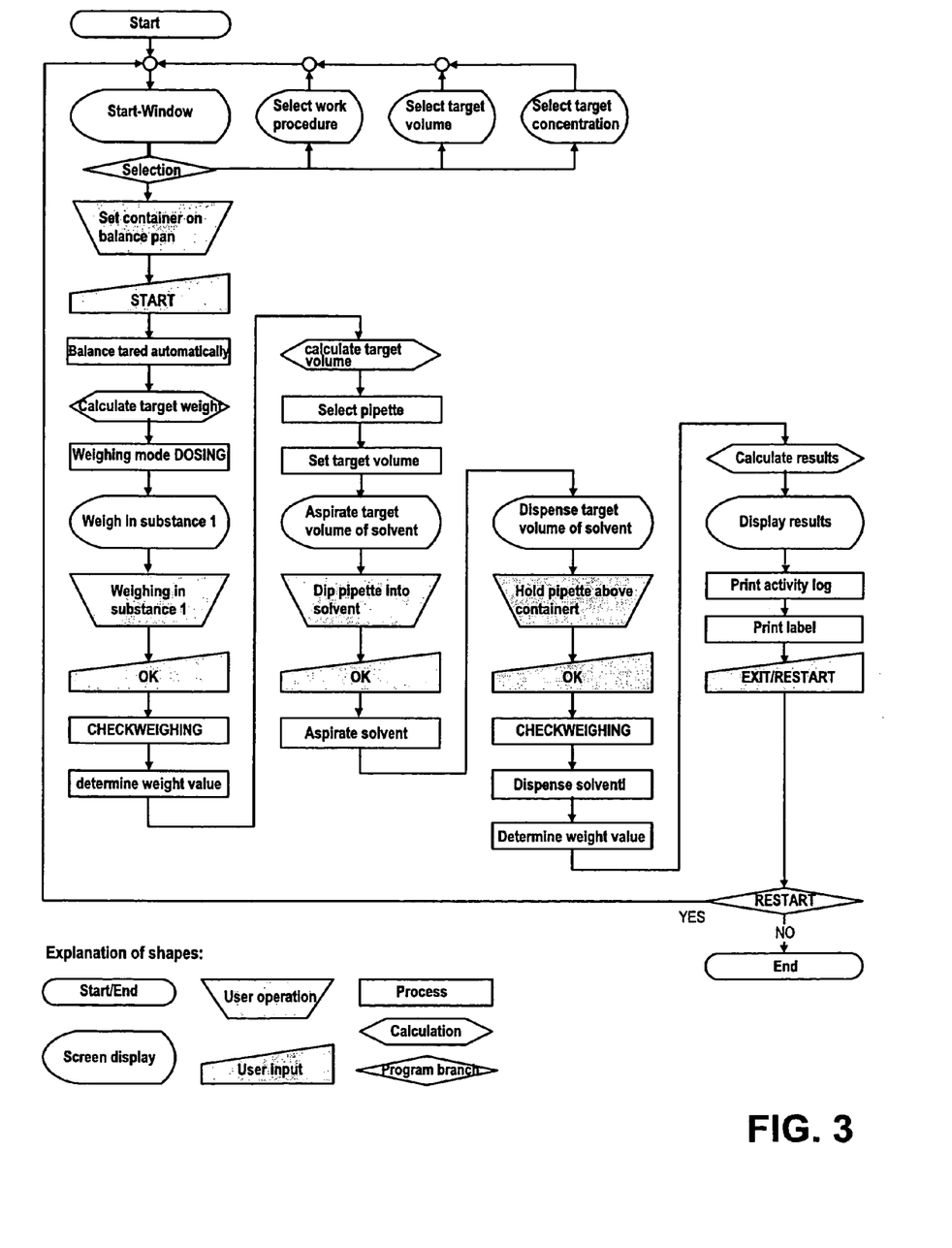
FIG. 3 represents an exemplary detailed sequence of operations for the preparation of a chemical solution by means of a method as disclosed herein.

The flowchart of FIG. 3 represents an example for the detailed sequence of steps of a program for preparing a chemical solution of a solid with a liquid through a method in accordance with the invention. In particular, the differently shaped flowchart blocks in FIG. 3 represent a distinction between different types of actions, i.e., whether an operation is performed by an attendant or by the program, whether the operation represents a computing step, or an interaction between the attendant and the program by means of the display and operating unit 4 of the balance 1. After the opening window appears on the display screen, the latter is updated in a sequence of steps in which the questions regarding the selection of the work procedure, the target volume and the target concentration are presented and have to be answered with an entry, which may additionally have to be acknowledged with a confirmation, before the program proceeds through the continuation of the method.

A program for the control of different work processes and for the required computations at a work station with a balance 1 and at least one electronic pipette 2, 2', 2" cooperates with the standard applications programs of the balance, also referred to as weighing modes such as "dosing" and "check-weighing", in the sense that the standard applications programs can be integrated in the work process at the program steps where they are needed.

Figure 4:
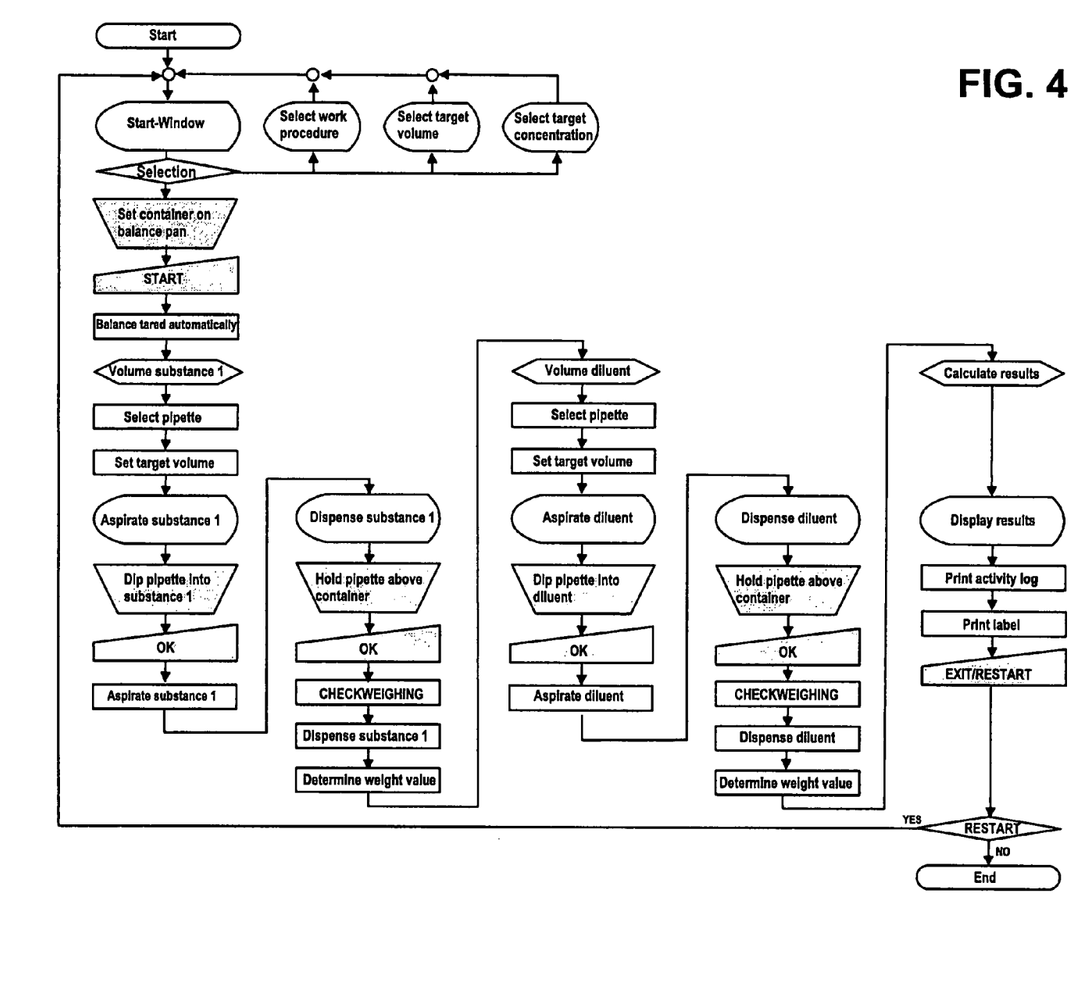
FIG. 4 represents an exemplary detailed sequence of operations for the preparation of a dilution by means of a method as disclosed herein.

The flowchart of FIG. 4 represents the detailed sequence of steps of a program for preparing a dilution of a liquid with another liquid in an analogous flowchart format as FIG. 3. The explanation given in FIG. 3 for the shapes of the different symbols applies likewise to FIG. 4. By weighing the substance that is to be diluted (substance 1), the method of FIG. 4 provides an accurate reference value, based on which the quantity of diluent can be calculated with a corresponding level of accuracy. The weight-based determination of the quantity of diluent can exceed the accuracy achievable with pipette-based measurements alone by up to three decimal orders. The high accuracy has the advantage that a high-order dilution can be performed in a single step where a conventional procedure would require a so-called dilution series, i.e., a series of steps in which the already diluted liquid is successively diluted again by the same factor until the desired low level of concentration has been attained. Thus, an exemplary method for preparing a dilution saves time, increases the degree of assurance, and avoids waste.

The processes of the foregoing description can be modified in a multitude of possible ways. For example, a verification step can be added to check whether the selected pipette 2, 2' or 2" is calibrated by looking up the calibration data in the memory unit 8 of the respective pipette before setting the target volume on a selected pipette 2'. It is further possible that there are frequent changes in the substances used in the aforementioned processes, or that new combinations of materials are used to prepare a solution of a solid with a liquid and/or a dilution of a fluid with another fluid. This will inevitably involve appropriate modifications in the work procedures. An exemplary program for preparing a solution of a solid with a liquid and/or a dilution of a liquid with another liquid lends itself well to such modifications, due to the aforementioned capability of freely configuring the work operations in the program.

Exemplary apparatuses and methods have been described and presented in foregoing embodiments. However the teachings herein will enable a skilled-in-the-art person to realize further embodiments. As a specific example, instead of an electronic pipette one could use a burette, or an electronic dispenser for the electronic dosage delivery device, for example if identical procedures are repeated within a short time span, in which case all of the solvent would be filled into the dispenser at once and the individual quantities set by the program would be dispensed sequentially for each of the procedures.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. An arrangement for preparing a solution of a solid with a liquid and/or a dilution of a liquid with another liquid, comprising:
    a balance comprising a weighing pan, a display- and operating unit, a processor, a storage memory, and a data interface; and
    a plurality of electronic pipettes, each pipette being equipped with a microprocessor, a memory unit, and a data interface, wherein a communication can be established between the data interface of the balance and the data interface of the at least one electronic pipette, wherein each electronic pipette has an identifier element that signals when the electronic pipette has been selected, and wherein the storage memory of the balance is encoded with a program executable for preparing a solution of a solid with a liquid and/or a dilution of a liquid in another liquid, said program being configured for performing calculations in the processor of the balance based on instructions input by an attendant, also based on substance data stored in the memory of the balance, said program being further configured for selecting an electronic pipette from the plurality of electronic pipettes and setting the electronic pipette for the liquid volume that is to be taken in and/or dispensed.

2. Arrangement according to claim 1, wherein a code reader is connected for communication with the balance, said code reader serving at least in part for entering data, and for identifying chemicals to be used.

3. Arrangement according to claim 1, comprising:
    a recording device configured as an activity log printer and/or a label printer interfaced with the balance.

4. Arrangement according to claim 1, wherein the storage memory of the balance comprises a database.

5. Arrangement according to claim 4, wherein the database holds substance data and/or substance parameters and/or work procedures.

6. Arrangement according to claim 1, wherein the balance is interfaced for communication with a laboratory information management system.

7. Arrangement according to claim 1, wherein the balance is interfaced with a data-processing system configured as a personal computer or a palmtop computer.

8. Arrangement according to claim 1, wherein the balance is interfaced with a computer in a computer network.

9. Arrangement according to claim 6, wherein a database resides in the laboratory information management system, and wherein substance data and/or substance parameters and/or work procedures are stored in the database.

10. Method for preparing a solution of a solid with a liquid and/or a dilution of a liquid with another liquid, wherein the method includes:
   connecting a balance comprising a display- and operating unit, a processor, a storage memory, and a data interface with a plurality of electronic the pipettes, each pipette being equipped with a microprocessor, a memory unit, a data interface, and an identifier element, wherein the balance and each electronic pipette can communicate with each other through their respective data interfaces, and wherein the storage memory of the balance is encoded with a program that performs calculations based on instructions given by the attendant, also based on substance data stored in the memory of the balance;
   wherein said program selects a pipette from the plurality of electronic pipettes, sets the pipette for the liquid volume that is to be taken in and/or dispensed; and
   activates the identifier element of the selected electronic pipette; and
   combining the solid and/or liquid substances to form the solution or dilution.

11. Method according to claim 10, wherein entry of instructions and confirmations by the attendant are performed using the display- and operating unit of the balance.

12. Method according to claim 10, wherein a database is available and wherein the balance which controls the dosage delivery device calls up work instructions, substance data and/or substance parameters from the database.

13. Method according to claim 10, wherein the balance measures a weight of a completed solution and/or dilution, and wherein a completed process of making a solution and/or dilution is subjected to a plausibility check.

14. Method according to claim 13, wherein a temperature of the solution is measured and used as an input parameter in calculations for the plausibility check.

15. Method according to claim 10, wherein a recording device is available and interfaced to the balance, and wherein said recording device generates an activity log of a completed and/or prematurely terminated preparation of a solution of a solid with a liquid and/or a dilution of a liquid with a further liquid.

16. Method according to claim 10, wherein a code reader is available and interfaced for communication with the balance, and wherein the code reader serves to scan data for use in the program.

17. Method according to claim 10, comprising the following acts performed by the attendant:
   selecting and obtaining chemicals for the solution and/or dilution to be prepared;
   calling up a work instruction on the display- and operating unit of the balance;
   calling up substance parameters on the display- and operating unit of the balance;
   entering a targeted concentration of the solution and/or dilution on the display- and operating unit of the balance;
   entering a targeted volume of the solution and/or dilution on the display- and operating unit of the balance;
   calling up a calculation routine on the display- and operating unit of the balance for a first substance to be weighed in;
   weighing a first substance into a container on the weighing pan;
   taking up a second substance using a pipette that has been selected and preset by the program and identified through a signal;
   delivering a volume that has been set on the pipette into the container that is sitting on the balance pan and contains the first substance; and
   entering a command for generating an activity log on the display- and operating unit of the balance.

18. Method according to claim 10, wherein a work procedure is freely configurable.

19. Method according to claim 10, wherein the balance is interfaced with a data-processing system and/or a computer in a computer network and/or a laboratory information management system whose respective memory is accessed by the balance to call up substance data and/or substance parameters for a solution that is currently to be prepared of a solid with a liquid and/or a dilution that is currently to be prepared of a liquid with another liquid, and to enter said substance data and/or substance parameters in the storage memory of the balance for use in calculations required under a current work procedure.

20. Method according to claim 19, wherein the data as well as an activity log of a completed solution- or dilution procedure are stored in a laboratory information management system, from which the data and/or the activity log are available for further use.

21. A balance comprising a weighing pan and a memory, the memory encoded with a program, wherein the program is configured to perform a work procedure selected by an attendant for preparing a solution of a solid with a liquid and/or a dilution of a liquid with another liquid, wherein the program is configured to perform calculations based on instructions entered by the attendant, based on substance data stored in the memory of the balance, and wherein the program is configured to select a pipette from a plurality of electronic pipettes, set the pipette for the liquid volume that is to be taken in and/or dispensed, and wherein the program is configured to activate an identifier element of the selected pipette.

22. The balance according to claim 21, wherein the program is configured to perform the following operations:
   converting a target concentration for a solution or a dilution from an entered unit of measure to a desired unit of measure compatible with the substance data and substance parameters;
   calculating an amount of liquid required for preparing a solution or dilution based on the weight of a first substance that has been measured with a balance;
   selecting a suitable electronic pipette and identifying the selected device;
   setting the selected electronic pipette for a volume dose to be taken in and/or dispensed;
   displaying a total weight and/or additional parameters in the display- and operating unit of the balance;
   after a second substance has been added, comparing its mass to the calculated values based on a volume that was set in the pipette and based on the stored density value, wherein the calculation takes temperature into account, for a gravimetric verification check of a completed solution;
   providing an indication of plausibility that a desired solution has been produced within a predefined tolerance window relative to a target volume and/or a target concentration; and
   generating a log record of the parameter settings and measured data.

23. Arrangement according to claim 7, wherein a database resides in the data processing system, and wherein substance data and/or substance parameters and/or work procedures are stored in the database.

24. Arrangement according to claim 8, wherein a database resides in the computer network, and wherein substance data and/or substance parameters and/or work procedures are stored in the database.

25. Arrangement according to claim 1, wherein the program is configured for performing calculations in the processor based on weighing results.

26. Method according to claim 10, wherein the program is configured for performing calculations in the processor based on weighing results.

27. The balance according to claim 21, wherein the program is configured to perform calculations based on obtained weighing results.

28. Arrangement according to claim 1, wherein the electronic pipette is constructed to aspirate the liquid.

29. Method according to claim 10, further comprising aspirating liquid into the at least one electronic pipette.

30. Arrangement according to claim 1, wherein the plurality of electronic pipettes comprises electronic pipettes with different volume capacities.

31. Method according to claim 10, wherein the plurality of electronic pipettes comprises electronic pipettes with different volume capacities.

32. The balance according to claim 21, wherein the plurality of electronic pipettes comprises electronic pipettes with different volume capacities.

33. Arrangement according to claim 1, wherein the identifier element is constructed to produce at least one of an optical signal and an audible signal when the electronic pipette is selected.

34. Method according to claim 10, wherein the identifier element produces at least one of an optical signal and an audible signal when activated.

* * * * *

UNITED STATES PATENT AND TRADEMARK OFFICE
CERTIFICATE OF CORRECTION

PATENT NO. : 7,651,664 B2 Page 1 of 1
APPLICATION NO. : 10/786580
DATED : January 26, 2010
INVENTOR(S) : Appoldt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1342 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,651,664 B2 |
| APPLICATION NO. | : 10/786580 |
| DATED | : January 26, 2010 |
| INVENTOR(S) | : Yvonne Appoldt et al. |

It is certified that error appears in the above-identified patent and that said Letters Patent is hereby corrected as shown below:

On the front page of the Letters Patent, under Assignee, please change:

"Mettler-Toledo GmbH" to --Mettler-Toledo AG--.

On the Title Page:

The first or sole Notice should read --

Subject to any disclaimer, the term of this patent is extended or adjusted under 35 U.S.C. 154(b) by 1342 days.

Claim 10, Column 13, Line 8 change "of electronic the pipettes," to --of electronic pipettes--.
Claim 12, Column 13, Lines 28-29 change "which controls the dosage delivery device calls," to --which controls the electronic pipettes calls--.
Claim 22, Column 14, Line 50, change "selected device;" to --selected pipette device--.

Signed and Sealed this
Twenty-second Day of February, 2011

David J. Kappos
*Director of the United States Patent and Trademark Office*